(12) United States Patent
Kuhner et al.

(10) Patent No.: US 7,494,810 B2
(45) Date of Patent: Feb. 24, 2009

(54) METHOD FOR ACCESSING MICROBIAL DIVERSITY

(75) Inventors: Carla H. Kuhner, Avondale, PA (US);
Barry Marrs, Kennett Square, PA (US);
James A. Romesser, Kennett Square, PA (US)

(73) Assignee: Franhofer USA Incorporated, Plymouth, MI (US)

( * ) Notice: Subject to any disclaimer, the term of this patent is extended or adjusted under 35 U.S.C. 154(b) by 0 days.

(21) Appl. No.: 10/349,335

(22) Filed: Jan. 22, 2003

(65) Prior Publication Data

US 2004/0038374 A1 Feb. 26, 2004

(51) Int. Cl.
*C12N 5/00* (2006.01)
*C12N 5/02* (2006.01)
*C12Q 1/00* (2006.01)
*C12Q 1/68* (2006.01)
*C07K 14/00* (2006.01)

(52) U.S. Cl. ............................... 435/373; 435/4; 435/6; 435/375; 530/350

(58) Field of Classification Search ............... 435/4, 435/7.1, 373, 6, 375; 530/350
See application file for complete search history.

(56) References Cited

OTHER PUBLICATIONS

Hentzer et al., 2002, Microbiology, vol. 148, p. 87-102.*
De Kievit et al., 1999, Science & Medicine, vol. 6, No. 6, p. 42-50.*
Bauer et al., 2002, Current Opinion in Biotechnology, vol. 13, p. 234-237.*
Branny et al., "Inhibition of Quorum Sensing by a *Pseudomonas aeruginosa* dksA Homologue," *Journal of Bacteriology*, Mar. 2001, vol. 183, No. 5, p. 1531-1539.
Lin et al., Acyl-Homoserine Lactone Acylase from *Ralstonia* Strain Xj12B Represents a Novel and Potent Class of Quorum-quenching Enzymes, *Molecular Microbiology*, Feb. 2003, vol. 47, No. 3, p. 849-860.
Guan et al., "Bacterial response to siderophore and quorum-sensing chemical signals in the seawater microbial community", BMC Microbiology, vol. 1, No. 27, (Oct. 23, 2001), pp. 1-11, URL, XP-002314547.

* cited by examiner

*Primary Examiner*—Shin-Lin Chen
(74) *Attorney, Agent, or Firm*—Drinker Biddle & Reath, LLP

(57) ABSTRACT

A method of interfering with quorum sensing regulation of genes to promote cell growth is disclosed. The method of is aimed at accessing microbial biodiversity. The method involves obtaining an environmental sample comprising at least one novel (uncultivated in the laboratory) microorganism, contacting the environmental sample with an effective amount of an agent or combination of agents which interferes with the quorum sensing regulation of genes, growing the treated sample in a culture medium containing the quorum sensing signal disrupting agent or agents, and analyzing the colonies of microorganisms grown to demonstrate genetic novelty.

6 Claims, No Drawings

METHOD FOR ACCESSING MICROBIAL DIVERSITY

BACKGROUND OF THE INVENTION

1. Field of the Invention

This invention relates to methods for accessing microbial diversity through disruption of microbial quorum sensing systems. In particular, this invention enables the isolation of novel microorganisms by dis-enabling quorum sensing systems that are used to maintain microbial cell density at a low level.

2. Description of Related Art

With recent developments in PCR technology and comparative microbial genome sequencing, it has been demonstrated in many environments that the number of microorganisms that have been cultured represents only a percentage of those present in a particular environment. It has been estimated that only approximately 1-5% of existing microorganisms have been cultured in the laboratory.

The organisms which remain "uncultivated" represent a potentially large pool of genes comprising novel microbial diversity. Accessing this diversity would allow the identification for example of enzymes exhibiting novel or enhanced biocatalytic characteristics, novel cofactors, or other novel secondary metabolites such as pharmaceuticals, polymers or other chemicals. Many industrial processes utilize (or could utilize) microbial processes or components thereof and could thus benefit greatly from the isolation of novel microorganisms exhibiting unique characteristics. In addition, novel microorganisms responsible for disease states could be identified. Also, environmental bioremediation could benefit greatly from the identification of microorganisms exhibiting novel biodegradation or bioconversion processes.

Many companies have recently been formed to access microbial diversity by using recombinant techniques to circumvent the inability to culture microorganisms. These techniques are limited in that they can only access single genes or small clusters of genes encoding short metabolic or biosynthetic pathways. The ability to cultivate a microorganism in the laboratory would provide a tremendous advantage.

In nature, bacteria communicate with one another in order to coordinate the expression of specific genes in a cell density-dependent manner. This bacterial communication is called quorum sensing, and it allows bacteria to control gene expression in response to the level of a diffusible signaling molecule called an autoinducer. The signaling molecule binds to a receptor protein, which then activates gene expression. Processes which are controlled by quorum sensing include virulence, bioluminescence, biofilm formation, swarming, sporulation, conjugal transfer of plasmids, and development of competence.

Three main types of quorum sensing systems have been described in bacteria: Type 1, Type 2 and peptide-based. Type 1 quorum sensing has thus far only been demonstrated in Gram negative microorganisms and utilizes acyl homoserine lactones as signaling molecules. Type 2 has been demonstrated in both Gram positive and Gram negative microorganisms and is believed to utilize 4-hydroxy-5-methyl-2H-furan-3-one or 4,5-dihydroxy-2-cyclopenten-1-one as the signaling molecule. Peptide-based quorum sensing systems have been demonstrated only in Gram positive microorganisms and rely on short peptides for gene activation. In addition, other chemical signals have been shown to be used for quorum sensing; these include gamma butyrolactone in *Streptomyces* sp. and 2-heptyl-3-hydroxy-4-quinolone in *Pseudomonas aeruginosa*.

Type 1 quorum sensing utilizes acyl homoserine lactones (AHSL) as signaling molecules. AHSL chemical signals consist of a lactone ring attached to an acyl chain by means of a peptide bond. The acyl chain length is specific for a given microorganism or for an AHSL-mediated process carried out by that microorganism. Some AHSLs contain a carbonyl or hydroxyl group at the 3 position of the acyl chain (e.g., 3-oxo-hexanoyl homoserine lactone, 3-hydroxy-butanoyl homoserine lactone). The paradigm for Type 1 quorum sensing is the *Vibrio fischeri* luxI/luxR system. The luxI protein catalyzes the synthesis of the autoinducer 3-oxo-hexanoyl homoserine lactone (OHHL). As the cell density increases the autoinducer accumulates and when a threshold level is reached, the OHHL signal interacts with the luxR protein. The luxR/OHHL complex binds to DNA at the lux box resulting in transcription of the bioluminescence genes. Other microorganisms exhibiting Type 1 quorum sensing possess analogs of luxI and luxR.

WO 01/85664 is incorporated in its entirety for its description of Type 2 quorum sensing. Biosynthesis of the Type 2 autoinducer is believed to proceed through progressive steps from methionine through S-adenosyl methionine to S-adenosyl homocysteine to S-ribosyl homocysteine to 4-hydroxy-5-methyl-2H-furan-3-one or 4,5-dihydroxy-2-cyclopenten-1-one. Enzymes involved in the synthesis are believed to include methionine adenosyl transferase, methyl transferase, nucleosidase and the luxS protein or its analogs, which synthesizes 4-hydroxy-5-methyl-2H-furan-3-one or 4,5-dihydroxy-2-cyclopenten-1-one from its precursor. In *Vibrio harveyi*, the receptors for the Type 2 autoinducer are luxP and luxPQ. When autoinducer concentrations reach a threshold level, the autoinducer interacts with the receptor and luxO is dephosphorylated (and inactivated), thereby preventing activation of a repressor and allowing luxR to activate transcription of the luxCDABE genes.

Many Gram positive bacteria use secreted peptides as autoinducers. Generally, in peptide based quorum sensing systems, the peptide is secreted by an ATP-binding cassette (ABC) transporter. The concentration of the autoinducer increases with cell density, and at a threshold level two component sensor kinases detect the autoinducer. A phoshorylation cascade is initiated which results in phosphorylation of a cognate response regulator protein. The response regulator is thus activated, allowing it to bind DNA and affect transcription of the quorum-sensing regulated genes.

In nature microorganisms regulate microbial processes in response to environmental conditions. In environments, for example, where nutrients are uniformly distributed, it is conceivable that microorganisms regulate cell division such that a high cell density is never achieved and cells remain dispersed; an example of such an environment is the ocean. It is possible that microorganisms utilize quorum sensing to control their cell division, and thus many microorganisms from these environments would thus far have been uncultivable in the laboratory due to quorum sensing. Therefore, if quorum sensing were disrupted or dis-enabled, novel microorganisms from these environments could be cultivated in the laboratory.

BRIEF DESCRIPTION OF THE INVENTION

Some bacteria produce chemical signals that regulate their own cell density. It has been suggested that quorum sensing signal molecules may inhibit the growth of daughter cells of the bacteria producing the quorum sensing signal molecules thereby poising the cell population at low density. Such a mechanism of sustaining a relatively low cell density may also contribute to the difficulties experienced by microbiologists in trying to establish pure cultures of these bacteria. Removal of the signal, blocking its production or inhibiting the activity of the signal may allow cell density to increase and thereby result in a "colony" or cell mass that can be visualized.

The present invention relates to a method of interfering with quorum sensing in order to inhibit the mechanism that regulates cell population growth. The method involves a) obtaining an environmental sample comprising at least one novel (uncultivated in the laboratory) microorganism, b) contacting the environmental sample with an effective amount of an agent or combination of agents that at least one of which interferes with, disrupts, removes, or dis-enables one or more quorum sensing signals in the environmental sample, c) growing the treated sample in a culture medium containing the quorum sensing disrupting agent or agents, and d) analyzing the colonies of microorganisms grown to demonstrate genetic novelty minimally at the species or subspecies level.

The invention allows for the capturing of previously unculturable microbial biodiversity.

DETAILED DESCRIPTION OF THE INVENTION

The invention relates to a method for accessing microbial diversity by interfering with or disrupting quorum sensing signals that regulate the population density of a microorganism by adding an agent or combination of agents that interferes with, disrupts, removes, or dis-enables the quorum sensing chemical signal system that regulates the population density of the microorganism. Where one of the words "interfering with, disrupting, removing, inhibiting or dis-enabling" appears in this specification the other words can be substituted.

The method of the present invention comprises: a) obtaining an environmental sample comprising at least one novel (uncultivated in the laboratory) microorganism, b) contacting the environmental sample with an effective amount of an agent or combination of agents that at least one of which interferes with, disrupts, removes, or dis-enables one or more quorum sensing signals in the environmental sample, c) growing the treated sample in a culture medium containing the quorum sensing signal disrupting agent or agents, and d) analyzing the colonies of microorganisms grown to demonstrate genetic novelty minimally at the species or subspecies level.

The environmental sample can be obtained from any source that is expected to contain at least one novel (i.e., not yet cultured) microorganism. Sources of the environmental sample expected to contain novel microorganisms include any body of water including but not limited to streams, rivers, lakes, ponds, swamps, oceans, and the like. Sources also include soil samples from any variety of sources. Soil samples can be taken from any type of forest, such as rain forest or deciduous. In addition, soil samples can be taken from grass lands, wet lands, tundra, dry arid regions, farm lands, the bottoms of lakes, rivers or oceans and the like. Samples may also be taken from geological formations, or environments exposed to extremes of temperature or pressure, including extraterrestrial environments. Examples of temperature extremes include but are not limited to the Arctic and Antarctic, or hydrothermal vents or hot springs. Samples may also be obtained from other microorganisms or multicellular organisms (including humans) containing microbial symbionts or pathogens; samples may also consist of bodily fluids. Environmental samples may also include, for example, plant components, such as leaves or the rhizosphere. Environmental samples may also include samples from industrial processes.

The invention relates to a method for interfering with, disrupting, removing, inhibiting or dis-enabling the acyl homoserine lactone (AHSL) chemical signals (autoinducers) which facilitate Type 1 quorum sensing in many Gram negative bacteria. AHSL signals may be disrupted using an agent that a) opens the lactone ring, b) hydrolyzes the peptide bond, or c) modifies the acyl chain.

In one embodiment of the invention, the agent is an enzyme that catalyzes a reaction with the acyl homoserine lactone autoinducer. Examples of classes of enzymes include esterases, lipases, lactonases, proteases, peptidases, aminoacylases or carboxypeptidases; many enzymes comprising these classes are commercially available.

It has been demonstrated that enzymes can degrade AHSLs. Lactonase has been shown to inactivate oxohexanoyl-, oxodecanoyl- and oxooctanoyl-homoserine lactones (Dong et al. PNAS USA 97:3526-331, 2000 and Nature 411: 813-817, 2001). Similarly, it has been demonstrated that a strain of Variovorax paradoxus can utilize several acyl homoserine lactones for growth; it is believed that the ring is enzymatically cleaved allowing the acyl chain and lactone ring to be used as sources of energy and nitrogen, respectively (Leadbetter and Greenberg, J. Bacteriology, 182:6921-6926). In another embodiment, the agent is a chemical other than an enzyme that catalyzes a reaction with the autoinducer molecule, such that the structure of the autoinducer is modified and the autoinducer becomes non-functional. Addition of sodium hydroxide or other base to raise the pH to greater than 8 is known to hydrolyze the lactone ring, thereby degrading the AHSL.

In one embodiment of the invention, the agent of the invention is a chemical that inhibits biosynthesis of the acylhomoserine lactone autoinducer, such as by inhibiting the luxI protein, an analog thereof, or a protein exhibiting a similar function. Examples of such an agent include cycloleucine or (2S,4S)-2-amino-4,5-epoxy pentanoic acid, inhibitors of S-adenosylmethionine synthesis. In another embodiment of the invention, the agent is a chemical that inhibits binding of the acyl homoserine lactone autoinducer to its receptor, thus blocking transcription of quorum sensing regulated genes. An example of such a chemical is an antibody that specifically binds to the receptor; the antibody may be polyclonal or monoclonal and can be prepared using methods that are well known in the art. An additional example of such a chemical is an analog of the AHSL itself. Halogenated furanones from the red alga Delisea pulchra which inhibit binding of the AHSL to the receptor that regulates swarming in Serratia liquefaciens are an example of an analog of an AHSL (Rasmussen, et al., Microbiology, 146:3237-3244, 2000).

In another embodiment of the invention, the invention relates to a method for interfering with, disrupting, removing, inhibiting or dis-enabling Type 2 quorum sensing. In one embodiment, the agent is an enzyme that catalyzes a reaction with the Type 2 quorum sensing autoinducer, 4-hydroxy-5-methyl-2H-furan-3-one, 4,5-dihydroxy-2-cyclopenten-1-one or an analog. In another embodiment, the agent is a chemical that disrupts the Type 2 autoinducer.

In yet another embodiment, the agent is a chemical that inhibits biosynthesis of the Type 2 quorum sensing autoinducer. Agents inhibiting the biosynthesis of the Type 2 autoinducer can modify the biosynthetic enzymes themselves. Alternatively the agent can be an analog of one of the biosynthetic precursors of one of the enzymes. For example, the agent can be an analog of methionine, S-adenosyl homocysteine, or S-ribosylhomocysteine, thus preventing binding of these molecules to the appropriate enzyme and biosynthesis of the autoinducer.

In another embodiment of the invention, the agent is a chemical that inhibits binding of the Type 2 quorum sensing autoinducer to its receptor. The agent can be a chemical that modifies luxP or luxQ, or proteins that carry out similar functions in other organisms. Similarly an agent can inhibit Type 2 quorum sensing by modifying luxO, luxR or the repressor protein, or any of the proteins that carry out similar functions in other organisms. The agent can also bind to the autoinducer receptor or other proteins involved in signal transduction between the autoinducer and the quorum sensing-controlled genes; an example is an antibody that binds to one of the proteins involved. In another embodiment, the agent can be an analog of the Type 2 autoinducer molecule, such as a modified furanone.

In another embodiment, the invention relates to a method of interfering with, disrupting, removing, inhibiting or dis-enabling peptide-regulated quorum sensing by Gram positive bacteria. Many Gram positive bacteria use secreted peptides as autoinducers. In one embodiment, quorum sensing by Gram positive bacteria is inhibited by an enzyme that catalyzes a reaction with the peptide autoinducer. Examples of such enzymes include but are not limited to proteases, peptidases and deaminases. In some Gram positive organisms, such as *Staphylococcus*, the peptide contains a thiolactone ring; these autoinducers may also be disrupted by an enzyme catalyzing a reaction with the thiol bond, such as a thiol reductase. In another embodiment of the invention, the agent is a chemical that disrupts the structure of the autoinducer peptide such as by modifying carboxyl or amide groups. In still another embodiment of the invention, the agent is an antibody that binds to the autoinducer peptide, thus preventing binding of the peptide to its receptor protein. The antibody may also bind an autoinducer propeptide, thus preventing post-translational processing to the active autoinducer. Peptide mimetics, such as β-peptides, may also inhibit binding of a peptide to its receptor.

In another embodiment of the invention, the agent is a chemical that inhibits the biosynthesis of the autoinducer peptide. The agent may, for example, inhibit transcription of the peptide or its propeptide (in the case of autoinducers that are post-translationally modified). The agent may inhibit the cleavage of the autoinducer peptide from its propeptide.

In another embodiment, the agent is a chemical that inhibits the binding of the peptide to its receptor protein. The agent may be a chemical or enzyme that modifies the receptor or binds to the receptor, thereby inactivating it; an example is an antibody specific for the receptor which disrupts binding of the autoinducer to the receptor. In another embodiment, the agent is an analog of the autoinducer peptide which binds to the receptor, thereby preventing binding of the autoinducer. Current Opinion in Microbiology 1999, 2:40-45, the entire contents of which is herein incorporated by reference, describes how an autoinducer for one bacterial species may act as an inhibitor for another. These peptides can be used as agents of inhibition in the present invention. There are numerous other references citing inhibitors that a person skilled in the art would recognize as being useful in the present invention.

Other quorum sensing autoinducer molecules have been described, such as gamma-butyrolactone from *Streptomyces* and 2-heptyl-3-hydroxy-4-quinolone from *Pseudomonas aeruginosa*. It is likely that additional quorum sensing systems have not yet been described. Using the methods described above, it would be possible for one skilled in the art to disrupt these quorum sensing systems in order to allow colony formation by organisms that regulate cell density by using quorum sensing.

Any combination of the agents can be used to interfere with, disrupt, remove, or dis-enable or inhibit quorum sensing. For a nonlimiting example, an agent for the Type 1 autoinducer, an agent for the Type 2 autoinducer and an agent for the peptide autoinducer can be mixed together and used on a given sample.

The quorum sensing inhibiting agents of the present invention are preferably soluble in water and may be applied or delivered with an acceptable carrier system. The composition may be applied or delivered with a suitable carrier system such that the agent may be dispersed or dissolved in a stable manner so that the agent, when it is administered directly or indirectly, is present in a form in which it is available in a particularly advantageous way.

Also, the separate agents of the present invention may be preblended or each component may be added separately to the same environment according to a predetermined dosage for the purpose of achieving the desired concentration level of the treatment components and so long as the components eventually come into intimate admixture with each other.

In another embodiment of the invention, the method of the invention comprises utilizing a physical device which acts to keep the concentration of the autoinducer below the threshold concentration required for the quorum sensing response. An example of the physical device may be a membrane or other solid support to which microorganisms can attach. The membrane is then continuously washed with growth medium to maintain the concentration of the diffusible autoinducer at a low concentration. The physical device may comprise a polymer or other solid support to which antibodies specific for the autoinducer or the autoinducer receptor protein are bound. The autoinducer is thus prevented from binding to its receptor and quorum sensing is inhibited. Any type of physical support can be used that would house the membrane or solid support contemplated by this invention. Examples of such physical devices may include, but are not limited to, ultrafiltration or diafiltration units or chromatography columns which could be used to house the appropriate membrane or solid support.

The culture medium used for growth of the treated samples can be any medium known to those skilled in the art. Preferably, the medium is derived from components comprising the environment from which the sample is taken. For example, a growth medium to isolate marine microorganisms preferably contains marine salts. A medium for growth of soil microorganisms may be derived from soil extract. Media can be supplemented with appropriate components in order to isolate microorganisms growing on a unique substrate or exhibiting a novel characteristic. The solid support used to isolate individual colonies can be agar, agar noble, Gel-Rite or any other solid support known to those skilled in the art. Strategies for the isolation and growth of microorganisms are described in part in The Prokaryotes (Martin Dworkin, ed., Springer-Verlag, NY, 1999).

In order to identify a microorganism as novel, the nucleic acid of the microorganism must be sequenced and compared to databases of known microorganisms. DNA sequencing can be done by a company or organization specializing in sequencing or can be done by the investigator using methods and equipment known in the art.

EXAMPLES

Example 1

Growth and Isolation of Novel Microorganisms: Utilization of Esterase Sigma E0887 to Degrade Homoserine Lactone (Type 1) Autoinducer Signals.

In this example water from a lake/reservoir is used as the source of microorganisms, however any source that is expected to exhibit a diversity of novel (i.e., not yet cultured) microorganisms may be used.

Water samples (approximately 1-2 liters) are obtained at a depth of 0-2 meters from Marsh Creek Lake (Downingtown, Pa.) and Spruce Run Reservoir (Clinton, N.J.); the samples are maintained at 4-20 C until used.

Agar media are prepared consisting of 1) filter-sterilized sample water, 0.5% Difco Agar Noble (Becton Dickinson, Sparks, Md.), and 0.05% Difco Bacto Peptone and 2) filter-sterilized sample water, 0.5% Difco Agar Noble, and 0.50% Difco Bacto Peptone. Preferably the agar and peptone are prepared at 4× concentration in sample water, sterilized and then diluted with filter-sterilized sample water to the appropriate volume. When necessary, the media are supplemented with 200 U/ml of filter-sterilized esterase (Sigma #E0887) or 200 U/ml of boiled, filter-sterilized esterase (esterase is boiled for 10 min at 100 C and then cooled) (200 U/ml=final concentration). In this example the esterase Sigma E0887 is used to degrade the signal, however other enzymes or inhibitors of the Type 1 system may be used.

The agar media are poured into Petri plates and either 1) pour plates are prepared or 2) the agar is allowed to solidify and samples are spread on the agar surface.

Three sets of water samples are prepared: a) sample water plus E0887 (E0887 is dissolved in deionized water and filter-sterilized; final concentration in sample water 200 U/ml), b) sample water plus boiled E0887 (dissolved in deionized water, filter-sterilized, boiled for 10 min, and cooled; final concentration 200 U/ml), and c) sample water plus an amount of sterile, deionized water equal to that added to samples a) and b). The samples are then diluted in successive 1:10 steps to $1 \times 10^{-4}$, and 0.1 ml aliquots of the dilutions are plated into (pour plates) or on to the surface of the agar media. The agar plates are then incubated for up to 10 days at 20-30 C, preferably in a humidity-controlled chamber to prevent evaporation. The number of aliquots at each dilution and for each medium is determined by the number of colonies required to obtain statistically relevant differences in colony-forming units (CFU) on the plates with and without E0887.

Colony formation during growth can be monitored with a dissecting microscope, or alternatively, an indicator dye such as 2,3,5-triphenyltetrazolium chloride (TTC; 0.005%) may enable better visualization of the colonies.

After incubation, colonies are counted on/in the plates. The number of CFU on the plates containing esterase E0887 should be significantly greater than those on the plates lacking E0887. The plates containing boiled E0887 should allow for determination of those organisms that utilize peptides/proteins for growth; the number of CFU on these plates may be similar to that for "medium minus E0887" due to the peptone in the medium.

Colonies from the "medium plus E0887" plates are suspended in sterile sample water and transferred to fresh medium+/−E0887. Those colonies that grow on "medium+ E0887", but not on "medium−E0887" are then submitted to Accugenix™/Acculab (Newark, Del.) (or a laboratory offering similar services) for DNA sequencing to determine if the microorganisms belong to new genera, species or subspecies (i.e., "novel").

Example 2

Growth and Isolation of Novel Microorganisms: Utilization of L-Selenomethionine or Adenine to Inhibit the Type 2 Autoinducer Signal.

In this example water from the Atlantic Ocean is used as the source of microorganisms, however any source that is expected to exhibit a diversity of novel (i.e., not yet cultured) microorganisms may be used.

Water samples (approximately 1-2 liters) are obtained at a depth of 0-2 meters from the Atlantic Ocean, 1 mile east of Ocean City, Md.; the samples are maintained at 4 C until used.

Agar media are prepared consisting of 1) filter-sterilized sample water, 0.5% Difco Agar Noble (Becton Dickinson, Sparks, Md.), and 0.05% Difco Bacto Peptone and 2) filter-sterilized sample water, 0.5% Difco Agar Noble, and 0.50% Difco Bacto Peptone. Preferably the agar and peptone are prepared at 4× concentration in sample water, sterilized and then diluted with filter-sterilized sample water to the appropriate volume. When necessary, the media are supplemented with 10 mM (final concentration) L-(+)-selenomethionine (Aldrich #473944) or 5 mM (final concentration) adenine (Sigma #A-8626) as inhibitors of the Type 2 autoinducer system. Additional inhibitors of the Type 2 system may also be used.

The agar media are poured into Petri plates and either 1) pour plates are prepared or 2) the agar is allowed to solidify and samples are spread on the agar surface.

Two sets of water samples are prepared: a) sample water plus L-selenomethionine or adenine (dissolved in deionized water and filter-sterilized; final concentration 10 mM or 5 mM, respectively), and b) sample water plus an amount of sterile, deionized water equal to that added with the inhibitor in sample a). The samples are then diluted in successive 1:10 steps to $1 \times 10^{-4}$, and 0.1 ml aliquots of the dilutions are plated into (pour plates) or on to the surface of the agar media. The agar plates are then incubated for up to 10 days at 10-18 C, preferably in a humidity-controlled chamber to prevent evaporation. The number of aliquots at each dilution and for each medium is determined by the number of colonies required to obtain statistically relevant differences in colony-forming units (CFU) on the plates with and without inhibitor.

Colony formation during growth can be monitored with a dissecting microscope, or alternatively, an indicator dye such as 2,3,5-triphenyltetrazolium chloride (TTC; 0.005%) may enable better visualization of the colonies.

After incubation, colonies are counted on/in the plates. The number of CFU on the plates containing inhibitor should be significantly greater than those on the plates lacking inhibitor.

Colonies from the "medium plus inhibitor" plates are suspended in sterile sample water and transferred to fresh medium+/−inhibitor. Those colonies that grow on "medium+ inhibitor", but not on "medium−inhibitor" are then submitted to Accugenix™/Acculab (Newark, Del.) (or a laboratory offering similar services) for DNA sequencing to determine if the microorganisms belong to new genera, species or subspecies (i.e., "novel").

Example 3

Growth and Isolation of Novel Microorganisms: Utilization of the Peptide Asp-Ile-Cys-Asn-Ala-Tyr-Phe to Inhibit the Gram Positive, Peptide-based Signaling System.

In this example soil is used as the source of microorganisms, however any source that is expected to exhibit a diversity of novel (i.e., not yet cultured) microorganisms may be used.

Soil samples (approximately 500 g) are obtained from the $O_h$ and $A_h$ horizons of a decidous forest; the samples are maintained at 4 C until used.

Portions of the soil samples are washed 1:1 in tap water, filtered through Whatman #1 filter paper to obtain "soil water" and filter-sterilized. Agar media are prepared consisting of 1) filter-sterilized soil water, 0.5% Difco Agar Noble (Becton Dickinson, Sparks, Md.), and 0.05% Difco Bacto Peptone and 2) filter-sterilized soil water, 0.5% Difco Agar Noble, and 0.50% Difco Bacto Peptone. Preferably the agar and peptone are prepared at 4× concentration in soil water, sterilized and then diluted with filter-sterilized soil water to the appropriate volume. When necessary, the media are supplemented with the peptide Asp-Ile-Cys-Asn-Ala-Tyr-Phe (</=10 mM [final concentration]) as an inhibitor of Gram positive quorum-sensing peptide(s).

The agar media are poured into Petri plates and either 1) pour plates are prepared or 2) the agar is allowed to solidify and samples are spread on the agar surface.

Portions of the soil samples are washed 1:1 in sterile tap water. Soil particles are allowed to briefly settle, and two sets of water samples are prepared: a) soil water plus filter-sterilized Asp-Ile-Cys-Asn-Ala-Tyr-Phe (</=10 mM [final concentration]), and b) soil water plus an amount of sterile, deionized water equal to that added with the inhibitor in sample a). The samples are then diluted in successive 1:10 steps to 1×10$^{-4}$, and 0.1 ml aliquots of the dilutions are plated into (pour plates) or on to the surface of the agar media. The agar plates are then incubated for up to 10 days at 10-18 C, preferably in a humidity-controlled chamber to prevent evaporation. The number of aliquots at each dilution and for each medium is determined by the number of colonies required to obtain statistically relevant differences in colony-forming units (CFU) on the plates with and without peptide inhibitor.

Colony formation during growth can be monitored with a dissecting microscope, or alternatively, an indicator dye such as 2,3,5-triphenyltetrazolium chloride (TTC; 0.005%) may enable better visualization of the colonies.

After incubation, colonies are counted on/in the plates. The number of CFU on the plates containing inhibitor should be significantly greater than those on the plates lacking inhibitor.

Colonies from the "medium plus inhibitor" plates are suspended in sterile soil water and transferred to fresh medium+/−inhibitor. Those colonies that grow on "medium+inhibitor", but not on "medium−inhibitor" are then submitted to Accugenix™/Acculab (Newark, Del.) (or a laboratory offering similar services) for DNA sequencing to determine if the microorganisms belong to new genera, species or subspecies (i.e., "novel").

Example 4

Growth and Isolation of Novel Microorganisms: Utilization of a Peptidase to Inhibit the Gram Positive, Peptide-based Signaling System.

In this example soil is used as the source of microorganisms, however any source that is expected to exhibit a diversity of novel (i.e., not yet cultured) microorganisms may be used.

Soil samples (approximately 500 g) are obtained from the $O_h$ and $A_h$ horizons of a decidous forest; the samples are maintained at 4 C until used.

Portions of the soil samples are washed 1:1 in tap water, filtered through Whatman #1 filter paper to obtain "soil water" and filter-sterilized. Agar media are prepared consisting of 1) filter-sterilized soil water, 0.5% Difco Agar Noble (Becton Dickinson, Sparks, Md.), and 0.05% Difco Bacto Peptone and 2) filter-sterilized soil water, 0.5% Difco Agar Noble, and 0.50% Difco Bacto Peptone. Preferably the agar and peptone are prepared at 4× concentration in soil water, sterilized and then diluted with filter-sterilized soil water to the appropriate volume. When necessary, the media are supplemented with a peptidase, such as the Type IV bacterial protease from *Streptomyces griseus* (Sigma #P6911) as an inhibitor of the Gram positive quorum-sensing peptide(s). The peptidase must demonstrate sufficient efficacy against the peptide at low temperature and low peptide concentration, and the peptidase preparation must not contain microbial inhibitors. The concentration of peptidase used for inhibition is determined empirically with purified peptide.

The agar media are poured into Petri plates and either 1) pour plates are prepared or 2) the agar is allowed to solidify and samples are spread on the agar surface.

Portions of the soil samples are washed well 1:1 in sterile tap water. Soil particles are allowed to briefly settle, and three sets of water samples are prepared: a) soil water plus filter-sterilized peptidase, b) soil water plus filter-sterilized, boiled peptidase (peptidase is boiled at 100 C and then cooled), and c) soil water plus an amount of sterile, deionized water equal to that added with the peptidase in samples a) and b). The samples are then diluted in successive 1:10 steps to 1×10$^{-4}$, and 0.1 ml aliquots of the dilutions are plated into (pour plates) or on to the surface of the agar media. The agar plates are then incubated for up to 10 days at 10-18 C, preferably in a humidity-controlled chamber to prevent evaporation. The number of aliquots at each dilution and for each medium is determined by the number of colonies required to obtain statistically relevant differences in colony-forming units (CFU) on the plates with and without peptidase.

Colony formation during growth can be monitored with a dissecting microscope, or alternatively, an indicator dye such as 2,3,5-triphenyltetrazolium chloride (TTC; 0.005%) may enable better visualization of the colonies.

After incubation, colonies are counted on/in the plates. The number of CFU on the plates containing the peptidase should be significantly greater than those on the plates lacking the peptidase.

Colonies from the "medium plus peptidase" plates are suspended in sterile soil water and transferred to fresh medium+/−peptidase. Those colonies that grow on "medium+peptidase", but not on "medium−peptidase" are then submitted to Accugenix™/Acculab (Newark, Del.) (or a laboratory offering similar services) for DNA sequencing to determine if the microorganisms belong to new genera, species or subspecies (i.e., "novel").

Example 5

Growth and Isolation of Novel Microorganisms: Utilization of Antibodies to Inhibit the Gram Positive, Peptide-based Signaling System.

In this example soil is used as the source of microorganisms, however any source that is expected to exhibit a diversity of novel (i.e., not yet cultured) microorganisms may be used.

Soil samples (approximately 500 g) are obtained from the $O_h$ and $A_h$ horizons of a decidous forest; the samples are maintained at 4 C until used.

Antibodies to either the "autoinducer propeptide" or to the peptide itself (the autoinducer propeptide is the protein which is cleaved by bacteria to produce the autoinducer) are prepared using known methods.

Portions of the soil samples are washed 1:1 in tap water, filtered through Whatman #1 filter paper to obtain "soil water" and filter-sterilized. Agar media are prepared consisting of 1) filter-sterilized soil water, 0.5% Difco Agar Noble (Becton Dickinson, Sparks, Md.), and 0.05% Difco Bacto Peptone and 2) filter-sterilized soil water, 0.5% Difco Agar Noble, and 0.50% Difco Bacto Peptone. Preferably the agar and peptone are prepared at 4× concentration in soil water, sterilized and then diluted with filter-sterilized soil water to the appropriate volume. When necessary, the media are supplemented with an antibody to the propeptide of the autoinducer or to the autoinducer peptide. The antibody binds to the autoinducer as it is secreted from the cells or to the propeptide, thus deactivating it. The antibody must demonstrate sufficient affinity for the peptide or propeptide at low temperature and low peptide/propeptide concentration, and the antibody preparation must not contain microbial inhibitors. The concentration of antibody used for inhibition is determined empirically with purified peptide or propeptide.

The agar media are poured into Petri plates and either 1) pour plates are prepared or 2) the agar is allowed to solidify and samples are spread on the agar surface.

Portions of the soil samples are washed well 1:1 in sterile tap water. Soil particles are allowed to briefly settle, and two sets of water samples are prepared: a) soil water plus filter-sterilized antibody, and b) soil water plus an amount of sterile, deionized water equal to that added with the antibody in sample a). The samples are then diluted in successive 1:10 steps to 1×10$^{-4}$, and 0.1 ml aliquots of the dilutions are plated into (pour plates) or on to the surface of the agar media. The agar plates are then incubated for up to 10 days at 10-18 C, preferably in a humidity-controlled chamber to prevent evaporation. The number of aliquots at each dilution and for each medium is determined by the number of colonies required to obtain statistically relevant differences in colony-forming units (CFU) on the plates with and without antibody.

Colony formation during growth can be monitored with a dissecting microscope, or alternatively, an indicator dye such as 2,3,5-triphenyltetrazolium chloride (TTC; 0.005%) may enable better visualization of the colonies.

After incubation, colonies are counted on/in the plates. The number of CFU on the plates containing the antibody should be significantly greater than those on the plates lacking the antibody.

Colonies from the "medium plus antibody" plates are suspended in sterile, soil water and transferred to fresh medium+/−antibody. Those colonies that grow on "medium+antibody", but not on "medium−antibody" are then submitted to Accugenix™/Acculab (Newark, Del.) (or a laboratory offering similar services) for DNA sequencing to determine if the microorganisms belong to new genera, species or subspecies (i.e., "novel").

Example 6

Growth and Isolation of Novel Microorganisms: Utilization of Solid-Phase-Bound Antibodies to Inhibit a Peptide-regulated Signaling System in Organisms of the Domain Archaea.

Antibodies to the autoinducer peptide are generated using methods known in the art. The antibodies are then bound to NHS-activated Sepharose (Amersham Pharmacia Biotech) via primary amino groups according to procedures developed by the manufacturer. A column is prepared containing the antibody-bound Sepharose. A sample is obtained from the sediment in a swamp. An anaerobic medium is prepared which consists of swamp water supplemented with 0.05% peptone, antibiotics (penicillin and tetracycline) and titanium citrate as the reductant. The swamp sample is added to the Sepharose column and organisms are allowed to bind for one hour. The medium is then continuously flushed over the column for up to 5 days. In this manner, the autoinducer will be removed by the antibody, contaminating microorganisms of the Domain Bacteria will be killed through inclusion of the antibiotics, and thus the novel Archaea will be selected for. Microorganisms attached to beads can then be plated onto anaerobic swamp water medium containing 0.5% Agar Noble in order to isolate the novel Archaea. Microorganisms from colonies are sequenced to determine their novelty as described in Example 1.

Example 7

Growth and Isolation of Novel Microorganisms: Utilization of a Continuous Flow-Device to Inhibit Quorum Sensing and Isolate Novel Oral Pathogens.

Hydroxyapatite discs coated with saliva are suspended in a 1-liter continuous flow reactor containing a growth medium appropriate for oral microorganisms (such as a dilute Nutrient Broth medium [0.05%]). Prior to beginning continuous flow, saliva (50 ml) is collected from human subjects and added to the reactor. Microorganisms from the saliva are allowed to bind to the hydroxyapatite discs for one hour. Following attachment, the discs are continuously washed with fresh medium for up to 5 days. In this manner, autoinducer will be continuously washed out and microorganisms will attach and grow on the hydroxyapatite discs. Following growth, microorganisms can be isolated on agar-containing growth medium; microorganisms can be identified by DNA sequencing as described in Example 1.

Those skilled in the art will recognize, or be able to ascertain using no more than routine experimentation, numerous equivalents to the specific embodiments described herein. Such equivalents are considered to be within the scope of this invention and are covered by the following claims.

What is claimed is:

1. A method of accessing bacterial diversity wherein the method comprises:
   a) obtaining an environmental sample comprising at least one novel (uncultivated in the laboratory) bacterium, wherein said environmental sample is selected from the group consisting of a body of water, a soil sample, a sample taken from a geological formation, a sample taken from an environment exposed to extreme temperature or pressure, and a plant component,
   b) contacting the environmental sample with an effective amount of an agent selected from the group consisting of an esterase, a lipase, a protease, and any combination thereof, wherein said agent interferes with, disrupts, removes, or disenables Type 1 quorum sensing in the environmental sample,
   c) growing the treated sample in a culture medium containing said agent,
   d) isolating colonies of bacteria grown in step (c); and
   e) analyzing the colonies of bacteria and identifying genetic novelty minimally at the species or subspecies level.

2. The method of claim 1, wherein the agent is an esterase that catalyzes a reaction with an acyl homoserine lactone autoinducer.

3. The method of claim 1, wherein said body of water is selected from the group consisting of a stream, a river, a lake, a pond, a swamp, an ocean, and any combination thereof.

4. The method of claim 1, wherein said soil sample is selected from the group consisting of a grass land, a wet land, a tundra, a dry arid region, a farm land, a bottom of a lake, a bottom of a river, a bottom of an ocean, and any combination thereof.

5. The method of claim 1, wherein said environment exposed to extreme temperature or pressure is selected from the group consisting of the Arctic, the Antarctic, a hydrothermal vent, a hot spring, and any combination thereof.

6. The method of claim 1, wherein said plant component is selected from the group consisting of a leaf, a rhizosphere, and any combination thereof.

* * * * *